United States Patent [19]

Rasmussen

[11] Patent Number: 5,459,053

[45] Date of Patent: Oct. 17, 1995

[54] USE OF RUMEN CONTENTS FROM SLAUGHTER CATTLE FOR THE PRODUCTION OF LACTIC ACID

[75] Inventor: Mark A. Rasmussen, McCallsburg, Iowa

[73] Assignee: The United States of America as represented by the Secretary of Agriculture, Washington, D.C.

[21] Appl. No.: 378,157

[22] Filed: Jan. 25, 1995

[51] Int. Cl.$^6$ .......................................................... C12P 7/56
[52] U.S. Cl. ........................ 435/139; 435/832; 435/854; 435/858; 435/885
[58] Field of Search ................................... 435/139, 885, 435/858, 854, 832

[56] References Cited

U.S. PATENT DOCUMENTS

| | | | |
|---|---|---|---|
| 3,857,971 | 12/1974 | Abdo et al. | 426/53 |
| 4,061,732 | 12/1977 | Muir et al. | 424/117 |
| 4,889,732 | 12/1989 | Cross | 426/319 |
| 5,173,430 | 12/1992 | Edwards et al. | 436/20 |

OTHER PUBLICATIONS

Gómez–Hernández, J., et al., "Lactic Acid Production Using Animal Wastes as Inoculum", *Biotechnology Letters*, vol. 5, No. 9, Sep. 1, 1983, pp. 629–632.

Klinger, I, et al., "Methanogenic Fermentation of Rumen Content in Slaughterhouse", *Isr. J. Vet. Med.*, vol. 42, No. 1, 1986, Abstract.

*Primary Examiner*—Herbert J. Lilling
*Attorney, Agent, or Firm*—M. Howard Silverstein; Randall E. Deck; John D. Fado

[57] ABSTRACT

A novel process for producing lactic acid using the rumen contents collected from slaughtered cattle or sheep is disclosed. The rumen contents are initially incubated for a period of time and under sufficiently low pH conditions effective to kill and/or inactivate non-lactic acid producing bacteria therein. Prior to or following this inactivation, the rumen contents are combined with a supplemental culture medium to form a fermentation broth and provide additional sources of carbohydrate and organic N for enhanced growth of lactic acid bacteria. In the second stage of the process, the fermentation broth is fermented under conditions promoting growth of the lactic acid bacteria to increase their cell mass to high densities. Optimal growth is attained by adjusting the pH of the fermentation broth to between about 6.6 to 7.2 and then incubating under anaerobic conditions for a sufficient time to lower its pH to between about 4.7 and 5.2. In the third stage of the process, once high cell densities are achieved, incubation of the fermentation broth is continued for a sufficient time with the pH maintained between about 4.7 and 5.2 to allow accumulation of lactic acid.

28 Claims, No Drawings

USE OF RUMEN CONTENTS FROM SLAUGHTER CATTLE FOR THE PRODUCTION OF LACTIC ACID

BACKGROUND OF THE INVENTION

1. Field of the Invention

The invention relates to a process for the production of lactic acid from the rumen contents of cattle or sheep collected during slaughter.

2. Description of the Prior Art

Waste from the slaughter of cattle and sheep poses a significant health and disposal problem for slaughter houses. Rumen contents, which comprise a substantial fraction of this waste, care currently of little if any value to the industry. Typically, slaughter plants collect the rumen contents from the animals as a separate by-product from the line. The line portion is removed and disposed of as liquid waste. In some locations, the solids may be spread on land or given to beef cattle feedlots. However, in other locations, slaughter plants must pay for disposal of the solids.

Lactic acid is used commercially in a wide variety of applications. Several of these applications include use in the textile industry as a mordant or solvent when dyeing and for reducing chromates in mordanting wool, as a confectionary, in cheese making, in brewing as an acidulant, in the tanning industry for dehairing, plumping and decalcifying hides, in pharmacy as an acidulant, irrigant or antiseptic, and in organic synthesis such as the manufacture of lactates [The Merck Index, Eleventh Edition, Budavari et al. (ed.), Merck & Co., Inc., Rahway, N.J., 1898, p. 5214].

Conventional processes for the manufacture of lactic acid have relied upon fermentation of carbohydrates by a number of different lactic acid bacteria or by direct chemical synthesis. The lactic acid bacteria are generally recognized as those gram-positive bacteria that produce lactic acid as a major or sole product of fermentative metabolism. They belong to the genera Lactobacillus, Streptoccoccus, Leuconostoc, and Pediococcus. Most commonly, these fermentations have employed cultures of Streptococci, or Lactobacilli such as *Lactobacillus delbrueckii, L. casei, L. bulgaricus* or *L. acidophilus,* or other bacteria such as *Bacillus acidilacti.* Traditional substrates used in these fermentations include milk, whey, cornstarch, potatoes and molasses.

Gomez-Hernandez and Coronado-Vega disclosed the production of lactic acid by anaerobic fermentation with a complex mixture of microorganisms as an inoculum [Biotechnology Letters, 5(9):629–632, (1983)]. Using cow manure to inoculate a culture medium, lactic acid production could be effected by maintaining the pH at relatively high levels.

SUMMARY OF THE INVENTION

I have now discovered a novel process for producing lactic acid using the rumen contents collected from slaughtered cattle or sheep. In the first or inactivation stage of the process, the rumen contents are incubated for a period of time and under sufficiently low pH conditions effective to kill and/or inactive most non-lactic acid producing bacteria therein. The elimination of these bacteria reduces the background competition for nutrients with the lactic acid bacteria during subsequent fermentation. Prior to or following this inactivation, the rumen contents are preferably combined with a supplemental culture medium to form a fermentation broth and provide additional carbohydrate and organic nitrogen for enhanced growth of lactic acid bacteria. In the second stage of the process, the fermentation broth is fermented under conditions promoting growth of the lactic acid bacteria to increase their cell mass to high densities. Optimal growth is attained by adjusting the pH of the fermentation broth to between about 6.6 to 7.2 and then incubating under anaerobic conditions for a sufficient time to lower its pH to between about 4.7 and 5.2. In the third stage of the process, once high cell densities are achieved, incubation of the fermentation broth is continued for a sufficient time with the pH maintained between about 4.7 and 5.2 to allow accumulation of lactic acid.

In accordance with this discovery, it is an object of this invention to provide a novel, inexpensive process for the production of lactic acid.

It is another object of this invention to provide a process for the production of lactic acid which does not require aseptic conditions or sterilization of media and equipment.

It is a further object of this invention to provide a process for conversion of a low value by-product or waste material of the slaughter house industry into a commercially valuable product, lactic acid.

These and other objects and advantages of the invention will become readily apparent from the ensuing description.

DETAILED DESCRIPTION OF THE INVENTION

The rumen contents used in the process of this invention serve as both the live microbial inoculum for the fermentation as well as an inexpensive source of nutrients critical to the growth of bacteria which produce lactic acid. In the course of processing cattle or sheep for meat production at commercial packing or slaughter houses, the animals are sacrificed, skinned and eviscerated. Typically, as each animal is gutted, valuable organs such as the liver, kidneys, and occasionally the rumen, are recovered and sold for human consumption, while the remaining organs and fluids are discarded. In accordance with this invention, the liquid rumen contents, that is the fluid material contained within the interior of the rumen, are not disposed of but are collected for use as described herein. Although the rumen contents also include solid material which may be optionally used together with the liquid rumen contents, the solids are not essential and may be removed by settling or straining, and discarded.

Following collection, the rumen contents may be used immediately for lactic acid production at the slaughter facility. Alternatively, the material may be stored for later use or shipped for use at another fermentation facility. The practitioner skilled in the art will recognize that if the material is stored, it should be at a suitable temperature and under anaerobic conditions effective to prevent overgrowth of undesirable bacteria. In any event, it will be apparent that the rumen contents should not be sterilized.

To commence the fermentation, the rumen contents are incubated in an anaerobic environment under conditions which are effective to select for growth of lactic acid producing bacteria therein. This is accomplished by lowering the pH of the rumen contents to a level sufficient to inactivate or kill non-lactic acid bacteria, usually by addition of a mineral or organic acid. With the pH maintained at this level, the rumen contents are incubated for a sufficient time to inactivate more than about 90%, and preferably more than about 95%, of the non-lactic acid producing bacteria present in the rumen contents. Removal of the predominant portion of non-lactic acid bacteria in this manner advances the subsequent homofermentative production of lactic acid without the production of substantial amounts of contaminating acids. While the specific pH level selected for this inactivation may be varied, it is preferably maintained within the range of between about 4.5 to 5.5, with a pH of about 5.0 being particularly preferred. The length of time for the incubation is not critical. However, the rumen contents are preferably incubated at the lowered pH for at least one generational period to insure that most rumen microorganisms are exposed to the inactivating pH for at least one complete cell division cycle. Without being limited thereto, a period of at least about 20 to 90 minutes is generally suitable.

While it is envisioned that the fermentation may be conducted using the rumen contents alone, that is, without addition of supplemental nutrients, growth of lactic acid bacteria and production of lactic acid may be greatly reduced. For optimal and lactic acid production, the rumen contents are preferably combined with a culture medium having supplemental sources of nitrogen and carbohydrates assimilable by the lactic acid bacteria, particularly *Streptococcus bovis*. Although this supplemental medium is preferably added prior to the inactivation stage described hereinabove, in the alternative it may be added subsequent to that stage. Without being limited thereto, suitable carbohydrate sources include glucose, wheat flour, corn starch, cane sugar molasses, beet sugar molasses, malt extract, cassava starch, sulfite waste liquor, whey and potato starch. A variety of nitrogen sources may be used as well, although optimal lactic acid yields have been obtained with organic nitrogen sources. Suitable nitrogen sources include but are not limited to Cas amino acids, casein, blood meal, corn steep liquor, yeast extract, soybean or alfalfa meal, or peptones (e.g., hydrolyzates of casein, meat, gelatin, soy meal or alfalfa meal). The amount of supplemental medium combined with the rumen contents is not critical, and varies with the particular media used. Generally, optimal lactic acid yields have been obtained using fermentation broths composed of about 80 to 90% supplemental medium and about 10 to 20% rumen contents, by volume.

In accordance with an optional but preferred embodiment, after the inactivation stage at low pH, the pH of the rumen contents may be raised to about 5.5 to about 6.5, and preferably to about 6.0, by the addition of an appropriate base, such as NaOH. The rumen contents are then incubated with the pH maintained at this level and under anaerobic conditions for a period of time sufficient to allow the lactic acid bacteria therein to become acclimated to higher pH conditions approaching those employed later in the fermentation. This acclimation stage also provides the dual advantage of continued inactivation of any remaining non-lactic acid bacteria. The length of this incubation period is not critical, but is preferably at least about 30 to 90 minutes.

In the second or growth stages of the process, the fermentation broth, composed of the rumen contents and supplemental culture medium, is fermented under conditions effective for promoting growth of the lactic acid bacteria to increase their cell mass to high densities. In the preferred embodiment, the pH of the fermentation broth is initially raised to between about 6.6 to 7.2, preferably to between about 6.8 to 7.0, and the broth is then incubated under anaerobic conditions, thereby allowing the lactic acid bacteria to grow under optimal conditions. Concurrent with this increase in the concentration of bacteria, lactic acid will be produced, gradually lowering the pH of the fermentation broth. The pH of the fermentation broth is allowed to drop to between about 4.7 and 5.2, preferably to about 5.0. The skilled practitioner will recognize that the duration of the incubation period will be contingent upon the time required for the pH to reach the above-mentioned range.

Once the pH of the fermentation broth has fallen to the prescribed level (i.e., between about 4.7 and 5.2), the fermentation is continued with the pH maintained within this range for a sufficient amount of time to allow accumulation of lactic acid. Lactic acid production is optimal within this defined pH range; further declines in pH would eventually inactivate the lactic acid bacteria and lactic acid production would cease, while higher pH levels would result in a mixed acid fermentation. The length of this accumulation stage is not critical, and may vary with the desired yield, culture medium, and fermentation conditions. However, because lactic acid production during batch fermentation will generally become asymptotic, often after about 24 hours, the accumulation stage is preferably concluded after about 18 to 48 hours.

The fermentation is preferably conducted as a batch process, with agitation. All stages described hereinabove, including the inactivation, growth, lactic acid production, and optional acclimation stages, are conducted under anaerobic conditions. Use of a $CO_2$ atmosphere is preferred, as fermentations conducted in a $N_2$ atmosphere have exhibited reduced yields. Control or maintenance of the pH in the course of the fermentation may be accomplished using manual or automatic techniques conventional in the art, such as using automatic pH controllers for adding base or acid. Preferred bases employed for pH control include but are not limited to NaOH, $NH_4OH$ and $Ca(OH)_2$. The temperature of each stage is not critical, although it is understood that the temperature should be suitable for growth of lactic acid bacteria, generally between about 30° to 50° C., preferably between about 35° to 45° C., and particularly about 39° C. Neither the fermentor nor the supplemental culture medium need be sterilized prior to use.

At the completion of the fermentation, accumulated lactic acid may be recovered from the fermentation broth using conventional techniques. Without being limited thereto, suitable recovery techniques are described by L. E. Casida, Jr. (Industrial Microbiology, John Wiley and Sons, Inc., New York, 1968, pp. 304–314, especially at pp. 312–313), and L. B. Lockwood (Production of Organic Acids by Fermentation, In: *Microbial Technology*, second edition, vol. 1, ed. by H. J. Peppler et al., Academic Press, 1979, pp. 375–376), the contents of each of which are incorporated by reference herein. The particular recovery step selected will be contingent upon the culture medium used and the desired degree of purity of the lactic acid.

The lactic acid produced herein may be employed in a wide variety of well-known uses. Examples of potential uses include: as a disinfectant; dehairing and deliming hides; as a mordant and/or dye solvent in the textile industry; as an acidulant or preservation in the food and beverage industry; the preparation of polymers such as polylactides for various resins and biodegradable plastics; the preparation of calcium lactate for use in foods, and as a feed supplement.

The following examples are intended only to further illustrate the invention and are not intended to limit the scope of the subject matter which is defined by the claims.

EXAMPLE 1

Initial Inoculum

The inoculum was obtained from adult beef cattle during slaughter. As each animal was sacrificed, the rumen was removed and its content collected. Solids were removed from the contents and discarded. The remaining fresh rumen fluid was used as inoculum as described hereinbelow.

Fermentation Apparatus

Fermentations were conducted in a batch-type fermentor equipped with an automatic temperature controller, a vane or inert gas agitator with $CO_2$ gas supply, and an automatic pH controller (±0.1 pH units) with pH probe and metering pump for addition of acid or base solutions. Throughout the fermentation, the pH was continuously monitored and the temperature was maintained at 39° C.±0.2° C. Anaerobic conditions were maintained by flushing the vessel with a constant stream of $O_2$-free $CO_2$.

Supplemental Culture Medium

One l of supplemental culture medium was prepared in the fermentor from the following components:

| aqueous mineral solution #1 | 75 ml |
|---|---|
| 6 g $K_2HPO_4$/l | |
| aqueous mineral solution #2 | 75 ml |
| 6 g $KH_2PO_4$/l | |
| 6 g $(NH_4)_2SO_4$/l | |
| 12 g NaCl/l | |
| 2.5 g $MgSO_4$ with 7 $H_2O$/l | |
| 1.6 g $CaCl_2$/l | |
| water | 850 ml |
| wheat flour | 150 g |
| casein | 5 g. |

The medium in the fermentor was bubbled with $CO_2$ gas to saturation and 10 ml of $Na_2S$ solution (2.5% w/v, prepared and stored under $N_2$ gas) was added. The medium was allowed to stabilize at 39° C. with agitation.

Fermentation

One hundred ml of fresh rumen fluid was added to 1 l of the supplemental culture medium in the fermentor under anaerobic conditions. The pH was lowered to 5.0 by addition of approximately 0.3 ml concentrated sulfuric acid per l of the fermentation broth (combined rumen contents and culture medium). The pH was maintained at this level for 1 hr, resulting in the inactivation of more than 95% of the non-lactic acid bacteria.

After incubation at pH 5.0 for 1 hr, the pH of the fermentation broth was increased to 6.0 by addition of 5N NaOH. The pH was maintained at this level for 1 hr.

Following the incubation at pH 6.0, 50 ml/l of $Na_2CO_3$ (8% w/v solution in water) was added, and the pH of the fermentation broth was increased to 6.8–7.0 by addition of 5N NaOH. The fermentation was allowed to proceed without pH control until the pH of the fermentation broth reached 5.0 as a result of lactic acid production. After the pH decreased to 5.0, it was maintained at this level and the fermentation continued with pH control to the endpoint of 48 hours.

Lactate yields were monitored throughout the course of the fermentation and are shown in Table 1. The final lactate concentration in the fermentation broth was 825 mM (approximately 74 g lactate/l).

EXAMPLE 2

In two separate trials, the process of example 1 was repeated except that the relative amount of rumen fluid to supplemental medium was changed to 5% and 30% rumen fluid (v/v). In each instance, final lactate yields were significantly reduced, to 480 mM and 550 mM, respectively.

EXAMPLE 3

The process of example 1 was repeated except that glucose and trypticase were substituted for the wheat flour and casein, respectively. At the conclusion of the fermentation, the lactate yield was 700 mM (approximately 63 g/l).

It is understood that the foregoing detailed description is given merely by way of illustration and that modifications and variations may be made therein without departing from the spirit and scope of the invention.

TABLE 1

| Production of lactic acid using rumen contents | |
|---|---|
| Hour of Fermentation | Concentration of lactate mM |
| 0 | 0 |
| 4.25 | 148 |
| 8.25 | 378 |
| 11.25 | 486 |
| 22.50 | 728 |
| 24.0 | 735 |
| 48.0 | 825 |

I claim:

1. A process for producing lactic acid comprising:
   (a) lowering the pH of rumen contents which have been collected from cattle or sheep during slaughter to a sufficient level and incubating under anaerobic conditions for a sufficient time to inactivate more than about 90% of non-lactic acid producing bacteria;
   (b) combining said rumen contents with a supplemental culture medium to form a fermentation broth;
   (c) adjusting the pH of said fermentation broth to between about 6.6 to 7.2 and incubating under anaerobic conditions for a sufficient time to allow the growth of lactic acid bacteria and production of lactic acid to lower the pH of said fermentation broth to between about 4.7 and 5.2, wherein said lactic acid bacteria are gram-positive bacteria that produce lactic acid as a major or sole product of fermentative metabolism;
   (d) maintaining the pH of said fermentation broth between about 4.7 and 5.2 while incubating for a sufficient time allow accumulation of lactic acid.

2. A process as described in claim 1 wherein said pH in step (a) is between about 4.5 to 5.5.

3. A process as described in claim 2 wherein said time in step (a) is at least about 20 minutes.

4. A process as described in claim 3 wherein said time in step (a) is about 1 hour.

5. A process as described in claim 1 wherein said supplemental culture medium comprises a carbohydrate and a source of organic nitrogen.

6. A process as described in claim 1 wherein said fermentation broth is comprised of about 80 to 90% by volume of said supplemental medium and about 10 to 20% by volume of said rumen contents.

7. A process as described in claim 1 wherein said time in step (d) is at least about 18 hours.

8. A process as described in claim 1 wherein said pH in step (d) is about 5.0.

9. A process as described in claim 1 further comprising raising the pH of the rumen contents to about 5.5 to about 6.5 after step (a) and prior to step (c), and incubating under anaerobic conditions.

10. A process as described in claim 9 wherein said rumen contents are incubated at said pH of about 5.5 to about 6.5 for at least about 30 minutes.

11. A process as described in claim 1 further comprising recovering said lactic acid produced in step (d).

12. A process as described in claim 1 wherein said rumen contents comprise the rumen fluid.

13. A process as described in claim 12 wherein said rumen contents consist essentially of said rumen fluid.

14. A process as described in claim 1 wherein said rumen contents are from cattle.

15. A process for producing lactic acid comprising:
   (a) combining rumen contents which have been collected from cattle or sheep during slaughter with a supplemental culture medium to form a fermentation broth;
   (b) lowering the pH of said fermentation broth to a sufficient level and incubating under anaerobic conditions for a sufficient time to inactivate more than about 90% of non-lactic acid producing bacteria;
   (c) adjusting the pH of said fermentation broth to between about 6.6 to 7.2 and incubating under anaerobic conditions for a sufficient time to allow the growth of lactic acid bacteria and production of lactic acid to lower the pH of said fermentation broth to between about 4.7 and 5.2, wherein said lactic acid bacteria are gram-positive bacteria that produce lactic acid as a major or sole product of fermentative metabolism;
   (d) maintaining the pH of said fermentation broth between about 4.7 and 5.2 while incubating for a sufficient time allow accumulation of lactic acid.

16. A process as described in claim 15 wherein said pH in step (b) is between about 4.5 to 5.5.

17. A process as described in claim 16 wherein said time in step (b) is at least about 20 minutes.

18. A process as described in claim 17 wherein said time in step (b) is about 1 hour.

19. A process as described in claim 15 wherein said supplemental culture medium comprises a carbohydrate and a source of organic nitrogen.

20. A process as described in claim 15 wherein said fermentation broth is comprised of about 80 to 90% by volume of said supplemental medium and about 10 to 20% by volume of said rumen contents.

21. A process as described in claim 15 wherein said time in step (d) is at least about 18 hours.

22. A process as described in claim 15 wherein said time in step (d) is about 5.0.

23. A process as described in claim 15 further comprising raising the pH of the rumen contents to about 5.5 to about 6.5 after step (b) and prior to step (c), and incubating under anaerobic conditions.

24. A process as described in claim 23 wherein said rumen contents are incubated at said pH of about 5.5 to about 6.5 for at least about 30 minutes.

25. A process as described in claim 15 further comprising recovering said lactic acid produced in step (d).

26. A process as described in claim 15 wherein said rumen contents comprise the rumen fluid.

27. A process as described in claim 26 wherein said rumen contents consist essentially of said rumen fluid.

28. A process as described in claim 15 wherein said rumen contents are from cattle.

* * * * *